(12) United States Patent
Simon et al.

(10) Patent No.: US 6,990,368 B2
(45) Date of Patent: Jan. 24, 2006

(54) METHOD AND APPARATUS FOR VIRTUAL DIGITAL SUBTRACTION ANGIOGRAPHY

(75) Inventors: David A. Simon, Boulder, CO (US); Kevin Foley, Germantown, TN (US); Mark Hunter, Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 525 days.

(21) Appl. No.: 10/116,631

(22) Filed: Apr. 4, 2002

(65) Prior Publication Data

US 2003/0191394 A1 Oct. 9, 2003

(51) Int. Cl.
*A61B 5/05* (2006.01)
*A61B 6/00* (2006.01)

(52) U.S. Cl. .......................................... 600/425; 378/21
(58) Field of Classification Search ................ 600/425, 600/408, 411, 415, 416, 417, 419, 426, 427, 600/428, 429; 378/21, 23, 25; 382/128
See application file for complete search history.

(56) References Cited

U.S. PATENT DOCUMENTS

| | | | |
|---|---|---|---|
| 1,576,781 | A | 3/1926 | Philips |
| 1,735,726 | A | 11/1929 | Bornhardt |
| 2,407,845 | A | 9/1946 | Nemeyer |

(Continued)

FOREIGN PATENT DOCUMENTS

| | | |
|---|---|---|
| CA | 964149 | 3/1975 |
| DE | 3042343 | 6/1982 |
| DE | 3508730 | 9/1986 |

(Continued)

OTHER PUBLICATIONS

Adams, L., et al., Aide au Reperage Tridimensionnel pour la Chirurgie de la Base du Crane, Innov. Tech. Biol. Med., vol. 13, No. 4, pp. 409–424 (1992).

Afshar, F. et al., A Three–Dimensional Reconstruction of the Human Brain Stem, Journal of Neurosurgery, vol. 57, No. 3, pp. 491–495 (Oct. 1982).

Awwad, E. et al., MRI Imaging of Lumber Juxtaarticular Cysts, Journal of Computer Assisted Tomography, pp. 415–417, vol. 14, No. 3 (May 1990).

Bajcsy, et al., Computerized Anatomy Atlas of the Human Brain, NCGA '81 Conference Proceedings, Second Annual Conference & Exhibition, Baltimore, MD, pp. 435–441 (Jun. 1981).

Barrick, E. F., Journal of Orthopaedic Trauma: Distal Locking Screw Insertion Using a Cannulated Drill Bit: Technical Note, Raven Press, vol. 7, No. 3, pp. 248–251 (1993).

(Continued)

*Primary Examiner*—Daniel Robinson
(74) *Attorney, Agent, or Firm*—Harness, Dickey & Pierce, P.L.C.

(57) ABSTRACT

A medical imaging system is provided that detects any change in relative position between the patient and the imaging device and corrects the image data for any motion that occurs. The medical imaging system includes: an imaging device for capturing two or more image data sets representative of a patient; a tracking subsystem for capturing patient position data that is indicative of the position of the patient and device position data that is indicative of the position of the imaging device; an image subtraction subsystem for performing a digital subtraction operation between at least two image data sets; and a motion correction subsystem configured to detect a change in the relative position between the patient and the imaging device and, upon detecting a change in the relative position, compensate in at least one of the first image data set and the second image data set for the change in relative position prior to performing the digital subtraction operation.

26 Claims, 6 Drawing Sheets

U.S. PATENT DOCUMENTS

| | | |
|---|---|---|
| 2,650,588 A | 9/1953 | Drew |
| 2,697,433 A | 12/1954 | Zehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |
| 3,847,157 A | 11/1974 | Caillouette et al. |
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab |
| 4,068,556 A | 1/1978 | Foley |
| 4,071,456 A | 1/1978 | McGee et al. |
| 4,117,337 A | 9/1978 | Staats |
| 4,173,228 A | 11/1979 | Van Steenwyk et al. |
| 4,202,349 A | 5/1980 | Jones |
| 4,228,779 A | 10/1980 | Wetzel |
| 4,259,725 A | 3/1981 | Andrews et al. |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,335,427 A | 6/1982 | Hunt et al. |
| 4,339,953 A | 7/1982 | Iwasaki |
| 4,341,220 A | 7/1982 | Perry |
| 4,358,856 A | 11/1982 | Stivender et al. |
| 4,360,028 A | 11/1982 | Barbier et al. |
| 4,368,536 A | 1/1983 | Pfeiler |
| 4,396,885 A | 8/1983 | Constant |
| 4,403,321 A | 9/1983 | Kruger |
| 4,418,422 A | 11/1983 | Richter et al. |
| 4,422,041 A | 12/1983 | Lienau |
| 4,431,005 A | 2/1984 | McCormick |
| 4,465,069 A | 8/1984 | Barbier et al. |
| 4,467,146 A | 8/1984 | Lassaux |
| 4,485,815 A | 12/1984 | Amplatz |
| 4,506,676 A | 3/1985 | Duska |
| 4,533,946 A | 8/1985 | Yasuhara et al. |
| 4,541,106 A | 9/1985 | Belanger et al. |
| 4,543,959 A | 10/1985 | Sepponen |
| 4,544,948 A | 10/1985 | Okazaki |
| 4,544,949 A | 10/1985 | Kurihara |
| 4,548,208 A | 10/1985 | Niemi |
| 4,559,557 A | 12/1985 | Keyes et al. |
| 4,572,198 A | 2/1986 | Codrington |
| 4,574,265 A | 3/1986 | Kaiser |
| 4,575,752 A | 3/1986 | Honda |
| 4,583,538 A | 4/1986 | Onik et al. |
| 4,584,577 A | 4/1986 | Temple |
| 4,586,926 A | 5/1986 | Osborne |
| 4,613,866 A | 9/1986 | Blood |
| 4,618,978 A | 10/1986 | Cosman |
| 4,621,628 A | 11/1986 | Bludermann |
| 4,625,718 A | 12/1986 | Olerud et al. |
| 4,628,355 A | 12/1986 | Ogura et al. |
| 4,639,867 A | 1/1987 | Suzuki et al. |
| 4,642,786 A | 2/1987 | Hansen |
| 4,645,343 A | 2/1987 | Stockdale et al. |
| 4,649,504 A | 3/1987 | Krouglicof et al. |
| 4,649,561 A | 3/1987 | Arnold |
| 4,651,732 A | 3/1987 | Frederick |
| 4,653,509 A | 3/1987 | Oloff et al. |
| 4,673,352 A | 6/1987 | Hansen |
| 4,689,670 A | 8/1987 | Okazaki |
| 4,692,864 A | 9/1987 | Shimoni et al. |
| 4,706,665 A | 11/1987 | Gouda |
| 4,719,419 A | 1/1988 | Dawley |
| 4,722,056 A | 1/1988 | Roberts et al. |
| 4,722,336 A | 2/1988 | Kim et al. |
| 4,724,110 A | 2/1988 | Arnold |
| 4,727,565 A | 2/1988 | Ericson |
| 4,729,379 A | 3/1988 | Ohe |
| 4,736,398 A | 4/1988 | Graeff et al. |
| 4,737,794 A | 4/1988 | Jones |
| 4,737,921 A | 4/1988 | Goldwasser et al. |
| 4,750,487 A | 6/1988 | Zanetti |
| 4,764,944 A | 8/1988 | Finlayson |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,213 A | 4/1989 | Cline et al. |
| 4,821,731 A | 4/1989 | Martinelli et al. |
| 4,829,373 A | 5/1989 | Leberl et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,870,692 A | 9/1989 | Zuiderveld et al. |
| 4,889,526 A | 12/1989 | Rauscher et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,578 A | 4/1991 | Greer et al. |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,454 A | 12/1991 | Griffith |
| 5,078,142 A | 1/1992 | Siczek et al. |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,142,939 A | 9/1992 | Bauer et al. |
| 5,152,288 A | 10/1992 | Hoenig et al. |
| 5,154,179 A | 10/1992 | Ratner |

| Patent No. | Date | Inventor(s) |
|---|---|---|
| 5,160,337 A | 11/1992 | Cosman |
| 5,161,536 A | 11/1992 | Vikomerson et al. |
| 5,172,115 A | 12/1992 | Kerth et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,189,690 A | 2/1993 | Samuel |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,229,935 A | 7/1993 | Yamagishi et al. |
| 5,230,338 A | 7/1993 | Allen et al. |
| 5,230,623 A | 7/1993 | Guthrie et al. |
| 5,233,990 A | 8/1993 | Barnea |
| 5,235,927 A * | 8/1993 | Singh et al. .............. 114/144 E |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,629 A | 11/1993 | Kitney et al. |
| 5,257,636 A | 11/1993 | White |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,276,927 A | 1/1994 | Day |
| 5,279,309 A | 1/1994 | Taylor et al. |
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,368,030 A | 11/1994 | Zinreich et al. |
| 5,369,678 A | 11/1994 | Chiu et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,442,674 A | 8/1995 | Picard et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,458,718 A | 10/1995 | Venkitachalam |
| 5,464,446 A | 11/1995 | Dreessen et al. |
| 5,478,341 A | 12/1995 | Cook et al. |
| 5,478,343 A | 12/1995 | Ritter |
| 5,480,422 A | 1/1996 | Ben-Haim |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,497,008 A | 3/1996 | Kumakhov |
| 5,503,416 A | 4/1996 | Aoki et al. |
| 5,513,637 A | 5/1996 | Twiss et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,551,431 A | 9/1996 | Wells, III et al. |
| 5,558,091 A | 9/1996 | Acker et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |

| | | | | | | |
|---|---|---|---|---|---|---|
| 5,603,318 A | | 2/1997 | Heilbrun et al. | 5,799,099 A | 8/1998 | Wang et al. |
| 5,611,025 A | | 3/1997 | Lorensen et al. | 5,800,352 A | 9/1998 | Ferre et al. |
| 5,617,462 A | | 4/1997 | Spratt | 5,800,535 A | 9/1998 | Howard, III |
| 5,617,857 A | | 4/1997 | Chader et al. | 5,802,719 A | 9/1998 | O'Farrell, Jr. et al. |
| 5,619,261 A | | 4/1997 | Anderton | 5,803,089 A | 9/1998 | Ferre et al. |
| 5,622,169 A | | 4/1997 | Golden et al. | 5,807,252 A | 9/1998 | Hassfeld et al. |
| 5,622,170 A | | 4/1997 | Schulz | 5,810,728 A | 9/1998 | Kuhn |
| 5,627,873 A | | 5/1997 | Hanover et al. | 5,810,735 A | 9/1998 | Halperin et al. |
| 5,628,315 A | | 5/1997 | Vilsmeier et al. | 5,812,629 A * | 9/1998 | Clauser ..................... 378/62 |
| 5,630,431 A * | | 5/1997 | Taylor ..................... 128/897 | 5,823,192 A | 10/1998 | Kalend et al. |
| 5,636,644 A | | 6/1997 | Hart et al. | 5,823,958 A | 10/1998 | Truppe |
| 5,638,819 A * | | 6/1997 | Manwaring et al. ........ 600/424 | 5,827,187 A | 10/1998 | Wang et al. |
| 5,640,170 A | | 6/1997 | Anderson | 5,828,725 A | 10/1998 | Levinson |
| 5,642,395 A | | 6/1997 | Anderton et al. | 5,829,444 A | 11/1998 | Ferre et al. |
| 5,643,268 A | | 7/1997 | Vilsmeier et al. | 5,831,260 A | 11/1998 | Hansen |
| 5,645,065 A | | 7/1997 | Shapiro et al. | 5,833,608 A | 11/1998 | Acker |
| 5,647,360 A | | 7/1997 | Bani-Hashemi et al. | 5,834,759 A | 11/1998 | Glossop |
| 5,647,361 A | | 7/1997 | Damadian | 5,836,954 A | 11/1998 | Heilbrun et al. |
| 5,651,047 A | | 7/1997 | Moorman et al. | 5,840,024 A | 11/1998 | Taniguchi et al. |
| 5,662,111 A | | 9/1997 | Cosman | 5,840,025 A | 11/1998 | Ben-Haim |
| 5,664,001 A | | 9/1997 | Tachibana et al. | 5,843,076 A | 12/1998 | Webster, Jr. et al. |
| 5,671,265 A | | 9/1997 | Andress | 5,848,967 A | 12/1998 | Cosman |
| 5,674,296 A | | 10/1997 | Bryan et al. | 5,851,183 A | 12/1998 | Bucholz |
| 5,676,673 A * | | 10/1997 | Ferre et al. ................. 606/130 | 5,865,846 A | 2/1999 | Bryan et al. |
| 5,681,260 A | | 10/1997 | Ueda et al. | 5,868,674 A | 2/1999 | Glowinski et al. |
| 5,682,886 A | | 11/1997 | Delp et al. | 5,868,675 A | 2/1999 | Henrion et al. |
| 5,682,890 A | | 11/1997 | Kormos et al. | 5,871,445 A | 2/1999 | Bucholz |
| 5,690,106 A | | 11/1997 | Bani-Hashemi et al. | 5,871,455 A | 2/1999 | Ueno |
| 5,690,108 A | | 11/1997 | Chakeres | 5,871,487 A | 2/1999 | Warner et al. |
| 5,694,945 A | | 12/1997 | Ben-Haim | 5,873,822 A | 2/1999 | Ferre et al. |
| 5,695,500 A | | 12/1997 | Taylor et al. | 5,884,410 A | 3/1999 | Prinz |
| 5,695,501 A | | 12/1997 | Carol et al. | 5,891,034 A | 4/1999 | Bucholz |
| 5,696,500 A | | 12/1997 | Diem | 5,891,157 A | 4/1999 | Day et al. |
| 5,697,377 A | | 12/1997 | Wittkampf | 5,904,691 A | 5/1999 | Barnett et al. |
| 5,702,406 A | | 12/1997 | Vilsmeier et al. | 5,907,395 A | 5/1999 | Schulz et al. |
| 5,711,299 A | | 1/1998 | Manwaring et al. | 5,913,820 A | 6/1999 | Bladen et al. |
| 5,713,946 A | | 2/1998 | Ben-Haim | 5,920,395 A | 7/1999 | Schulz |
| 5,715,822 A | | 2/1998 | Watkins | 5,921,992 A | 7/1999 | Costales et al. |
| 5,715,836 A | | 2/1998 | Kliegis et al. | 5,923,727 A | 7/1999 | Navab |
| 5,718,241 A | | 2/1998 | Ben-Haim et al. | 5,928,248 A | 7/1999 | Acker |
| 5,727,552 A | | 3/1998 | Ryan | 5,938,603 A | 8/1999 | Ponzi |
| 5,727,553 A | | 3/1998 | Saad | 5,938,694 A | 8/1999 | Jaraczewski et al. |
| 5,729,129 A | | 3/1998 | Acker | 5,947,981 A | 9/1999 | Cosman |
| 5,730,129 A | | 3/1998 | Darrow et al. | 5,950,629 A | 9/1999 | Taylor et al. |
| 5,730,130 A | | 3/1998 | Fitzpatrick et al. | 5,951,475 A | 9/1999 | Gueziec et al. |
| 5,732,703 A | | 3/1998 | Kalfas et al. | 5,954,647 A | 9/1999 | Bova et al. |
| 5,735,278 A | | 4/1998 | Hoult et al. | 5,954,796 A | 9/1999 | McCarty et al. |
| 5,738,096 A | | 4/1998 | Ben-Haim | 5,967,980 A | 10/1999 | Ferre et al. |
| 5,741,214 A | | 4/1998 | Ouchi et al. | 5,968,047 A | 10/1999 | Reed |
| 5,742,394 A | | 4/1998 | Hansen | 5,971,997 A | 10/1999 | Guthrie et al. |
| 5,744,953 A | | 4/1998 | Hansen | 5,976,156 A | 11/1999 | Taylor et al. |
| 5,748,767 A | | 5/1998 | Raab | 5,980,535 A | 11/1999 | Barnett et al. |
| 5,749,362 A | | 5/1998 | Funda et al. | 5,983,126 A | 11/1999 | Wittkampf |
| 5,749,835 A | | 5/1998 | Glantz | 5,987,349 A | 11/1999 | Schulz |
| 5,752,513 A | | 5/1998 | Acker et al. | 5,987,960 A | 11/1999 | Messner et al. |
| 5,755,725 A | | 5/1998 | Druais | 5,999,837 A | 12/1999 | Messner et al. |
| RE35,816 E | | 6/1998 | Schulz | 5,999,840 A | 12/1999 | Grimson et al. |
| 5,758,667 A | | 6/1998 | Slettenmark | 6,001,130 A | 12/1999 | Bryan et al. |
| 5,762,064 A | | 6/1998 | Polvani | 6,006,126 A | 12/1999 | Cosman |
| 5,767,699 A | | 6/1998 | Bosnyak et al. | 6,016,439 A | 1/2000 | Acker |
| 5,769,789 A | | 6/1998 | Wang et al. | 6,019,725 A | 2/2000 | Vesely et al. |
| 5,769,861 A | | 6/1998 | Vilsmeier | 6,024,695 A | 2/2000 | Taylor et al. |
| 5,772,594 A | | 6/1998 | Barrick | 6,050,724 A | 4/2000 | Schmitz et al. |
| 5,775,322 A | | 7/1998 | Silverstein et al. | 6,059,718 A | 5/2000 | Taniguchi et al. |
| 5,776,064 A | | 7/1998 | Kalfas et al. | 6,061,587 A * | 5/2000 | Kucharczyk et al. ....... 600/411 |
| 5,782,765 A | | 7/1998 | Jonkman | 6,063,022 A | 5/2000 | Ben-Haim |
| 5,787,886 A | | 8/1998 | Kelly et al. | 6,073,043 A | 6/2000 | Schneider |
| 5,792,055 A | | 8/1998 | McKinnon | 6,094,474 A | 7/2000 | Vezina |
| 5,795,294 A | | 8/1998 | Luber et al. | 6,104,944 A | 8/2000 | Martinelli |
| 5,797,849 A | | 8/1998 | Vesely et al. | 6,118,845 A | 9/2000 | Simon et al. |
| 5,799,055 A | | 8/1998 | Peshkin et al. | 6,122,538 A | 9/2000 | Sliwa, Jr. et al. |

| | | |
|---|---|---|
| 6,131,396 A | 10/2000 | Duerr et al. |
| 6,139,183 A | 10/2000 | Graumann |
| 6,149,592 A | 11/2000 | Yanof et al. |
| 6,156,067 A | 12/2000 | Bryan et al. |
| 6,161,032 A | 12/2000 | Acker |
| 6,167,296 A | 12/2000 | Shahidi |
| 6,167,445 A | 12/2000 | Gai et al. |
| 6,172,499 B1 | 1/2001 | Ashe |
| 6,175,756 B1 | 1/2001 | Ferre et al. |
| 6,223,067 B1 | 4/2001 | Vilsmeier |
| 6,233,476 B1 | 5/2001 | Strommer et al. |
| 6,246,231 B1 | 6/2001 | Ashe |
| 6,249,754 B1 | 6/2001 | Neul et al. |
| 6,273,896 B1 | 8/2001 | Franck et al. |
| 6,298,262 B1 | 10/2001 | Franck et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,356,617 B1 | 3/2002 | Besch et al. |
| 6,381,485 B1 | 4/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,463,318 B2 * | 10/2002 | Prince ........................ 600/420 |
| 6,470,207 B1 | 10/2002 | Simon et al. |
| 6,474,341 B1 | 11/2002 | Hunter et al. |
| 6,491,647 B1 * | 12/2002 | Bridger et al. .............. 600/585 |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,669,635 B2 * | 12/2003 | Kessman et al. ........... 600/437 |
| 6,675,037 B1 * | 1/2004 | Tsekos ........................ 600/417 |
| 6,690,965 B1 * | 2/2004 | Riaziat et al. .............. 600/428 |
| 6,694,162 B2 | 2/2004 | Hartlep |
| 6,701,179 B1 | 3/2004 | Martinelli et al. |
| 6,718,055 B1 * | 4/2004 | Suri ........................... 382/128 |

FOREIGN PATENT DOCUMENTS

| | | |
|---|---|---|
| DE | 3717871 | 12/1988 |
| DE | 3831278 | 3/1989 |
| DE | 3838011 | 7/1989 |
| DE | 3904595 | 4/1990 |
| DE | 3902249 | 8/1990 |
| DE | 4225112 | 12/1993 |
| DE | 4233978 | 4/1994 |
| DE | 4432890 | 3/1996 |
| DE | 19829230 | 3/2000 |
| DE | 10085137 | 11/2002 |
| EP | 0018166 | 10/1980 |
| EP | 0155857 A2 | 9/1985 |
| EP | 0 319 844 A1 | 1/1988 |
| EP | 0419729 A1 | 9/1989 |
| EP | 0350996 A1 | 1/1990 |
| EP | 350996 | 1/1990 |
| EP | 0359773 | 3/1990 |
| EP | 0 651 968 A1 | 8/1990 |
| EP | 0427358 | 5/1991 |
| EP | 0456103 | 11/1991 |
| EP | 0469966 | 2/1992 |
| EP | 0501993 | 9/1992 |
| EP | 0 581 704 B1 | 7/1993 |
| EP | 0655138 B1 | 8/1993 |
| EP | 0894473 A2 | 1/1995 |
| EP | 0908146 | 4/1999 |
| FR | 2417970 | 9/1979 |
| GB | 2094590 | 9/1982 |
| JP | 2765738 | 4/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/00702 | 1/1992 |
| WO | WO 92/03090 | 3/1992 |
| WO | WO 92/06645 | 4/1992 |
| WO | WO 94/04938 | 3/1994 |
| WO | WO 94/06352 | 3/1994 |
| WO | WO 94/23647 | 10/1994 |
| WO | WO 94/24933 | 11/1994 |
| WO | WO 96/11624 | 4/1996 |
| WO | WO 98/08554 | 3/1998 |
| WO | WO 98/38908 | 9/1998 |
| WO | WO 99/15097 | 4/1999 |
| WO | WO 99/21498 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/38449 | 8/1999 |
| WO | WO 99/60939 | 12/1999 |
| WO | WO 00/00086 | 1/2000 |
| WO | WO 01/30437 A1 | 5/2001 |

OTHER PUBLICATIONS

Batnitzky, S., et al., Three–Dimensional Computer–Reconstructions of Brain Lesions from Surface Contours Provided by Computed Tomography: A Prospectus, Neurosurgery, vol. 11, No. 1, Part 1, pp. 73–84 (1982).

Birg, W. et al., A Computer Programme System for Stereotactic Neurosurgery, Acta Neurochirurgica, Suppl. 24, pp. 99–108 (1977).

Boethius J. et al, Stereotactic Biopsies and Computer Tomography in Gliomas, Acta Neurochirurgica, vol. 49, pp. 223–232 (1978).

Boethius, J. et al., Stereotaxic Computerized Tomography With a GE 8800 Scanner, J. Neurosurg., vol. 52, pp. 794–800 (Jun. 1980).

Bouazza–Marouf et al., Robotic–Assisted Internal Fixation of Femoral Fractures, IMECHE, pp. 51–58 (1995).

Brack, C. et al., Accurate X–ray Based Navigation in Computer–Assisted Orthopedic Surgery, CAR '98, pp. 716–722.

Brack, C., et al., Towards Accurate X–Ray Camera Calibration in Computer–Assisted Robotic Surgery, CAR '96 Computer–Assisted Radiology, Proceedings of the International Symposium on Computer and Communication Systems for Image Guided Diagnosis and Therapy, Paris, pp. 721–728 (Jun. 1996).

Brunie, L. et al., Pre–and Intra–Irradiation Multimodal Image Registration: Principles and First Experiments, Radiotherapy and Oncology 29, pp. 244–252 (1993).

Bucholz, R. et al., A Comparison of Sonic Digitizers Versus Light Emitting Diode–Based Localization, Interactive Image–Guided Neurosurgery, Chapter 16, pp. 179–200.

Bucholz, R. et al., Image–Guided Surgical Techniques for Infections and the Trauma of the Central Nervous System, Neurosurgery Clinics of North America, vol. 7, No. 2, pp. 187–200 (Apr. 1996).

Bucholz, R. et al., The Correction of Stereotactic Inaccuracy Caused by Brain Shift Using an Intraoperative Ultrasound Device, CVRMed–MRCAS '97, First Joint Conference, Computer Vision, Virtual Reality and Robotics in Medicine and Medical Robotics and Computer–Assisted Surgery, pp. 459–466 (Mar. 19–22, 1997).

Bucholz, R. et al., Variables Affecting the Accuracy of Sterotactic Localization Using Computerized Tomography, Journal of Neurosurgery, vol. 79, pp. 667–673 (Nov. 1993).

Castleman, K. et al., Stereometric Ranging, Chapter 17: Three–Dimensional Image Processing, Digital Image Processing, pp. 364–369 (1979).

Champleboux, G., et al., Accurate Calibration of Cameras and Range Imaging Sensors: The NPBS Method, Proceedings 1992 IEEE International Conference on Robotics and Automation, pp. 1552–1557 (May 12–14, 1992).

Champleboux, G., Utilisation de Fonctions Splines pour la Mise au Point d'Un Capteur Tridimentionnel sans Contact (Jul. 1991).

Cinquin P., et al, Computer–Assisted Medical Interventions, pp. 63–65 (Sep. 1989).

Cinquin, P., et al., Computer–Assisted Medical Interventions, IEEE Engineering in Medicine and Biology, pp. 254–263 (May/Jun. 1995).

Clarysse, P., et al., A Computer–Assisted System for 3–D Frameless Localization in Stereotaxic MRI, IEEE Transactions on Medical Imaging, vol. 10., No. 4, pp. 523–529 (1991).

Colchester, A. et al., Information Processing Medical Imaging, 12.sup.th International Conference, IPMI, Lecture Notes in Computer Science, pp. 135–141 (1991).

Curry, Thomas S. III, M.D., et al., Christensen's Physics of Diagnostic Radiology, $4^{th}$ Edition, 1990.

Davatzikos, C. et al., Image Registration Based on Boundary Mapping, Thesis (Johns Hopkins University), pp. 1–30 (1995).

Feldmar, J. et al., 3D–2D Projective Registration of Free––Form Curves and Surfaces Rapport de recherche (Inria Sophia Antipolis), pp. 1–44 (1994).

Foley, J. D., et al. Fundamentals of Interactive Computer Graphics, Addison–Wesley Systems Programming Series, pp. 245–266 (1982).

Foley, K. T., et al., Image–Guided Intraoperative Spinal Localization, Intraoperative Neuroprotection, Chapter 19, pp. 325–340 (1996).

Foley, K. T., The SteathStation.TM., Three–Dimensional Image–Interactive Guidance of the Spine Surgeon, Spinal Frontiers, pp. 7–9 (Apr. 1996).

Frederick Barrick et al., Prophylactic Intramedullary Fixation of the Tibia for Stress Fracture in a Professional Athlete, Journal of Orthopaedic Trauma, vol. 6, No. 2, pp. 241–244 (1992).

Frederick et al., Technical Difficulties with the Brooker–Wills Nail in Acute Fractures of the Femur, Journal of Orthopaedic Trauma, vol. 6, No. 2, pp. 144–150 (1990).

Friston, K. et al., Plastic Tranformation of PET Images, Journal of Computer–Assisted Tomography, vol. 15, No. 4, pp. 634–639 (1991).

Gallen, C. et al., Intracranial Neurosurgery Guided by Functional Imaging, Surgical Neurology, vol. 42, pp. 523–530 (Dec. 1994).

Gildenberg, P. L., et al., Calculation of Stereotactic Coordinates from the Computed Tomographic Scan, CT Scan Stereotactic Coordinates, pp. 580–586 (May 1982).

Gonzalez, R. C. et al., Digital Image Fundamentals, Digital Image Processing, Second Edition, Addison–Wesley Publishing, pp. 52–54 (1987).

Gottesfeld–Brown, L. M. et al., Registration of Planar Film Radiographs with Computer Tomography, Proceedings of MMBIA, pp. 42–51 (Jun. 1996).

Gouda, K. et al., New Frame for Stereotaxic Surgery, Journal of Neurosurgery, vol. 53, pp. 256–259 (Aug. 1980).

Greitz, T. et al., Head Fixation System for Integration of Radiodiagnostic and Therapeutic Procedures, Neuroradiology, vol. 19, pp. 1–6 (1980).

Gueziec, A. P. et al., Registration of Computer Tomography Data to a Surgical Robot Using Fluoroscopy: A Feasibility Study, Computer Science/Mathematics, 6 pages (Sep. 27, 1996).

Hamadeh, A. et al., Automated 3–Dimensional Computer Tomographic and Fluoroscopic Image Registration, Computer Aided Surgery, 3: 11–19 (1998).

Hamadeh, A. et al., Towards Automatic Registration Between CT and X–Ray Images: Cooperation Between 3D/2D Registration and 2D Edge Detection, TIMC–IMAG Faculte de Medecine de Grenoble, pp. 39–46 (with 2 pages of drawings) (1995).

Hamadeh, A., et al., Kinematic Study of Lumbar Spine Using Functional Radiographies and 3D/2D Registration, TIMC UMR 5525—IMAG.

Hatch, J. F., Reference–Display System for the Integration of CT Scanning and the Operating Microscope, A Thesis Submitted to the Thayer School of Engineering, Dartmouth College, pp. 1–189 (Oct., 1984).

Heilbrun, M. P. et al., Stereotactic Localization and Guidance Using a Machine Vision Technique, Stereotactic and Functional Neurosurgery, vol. 58, pp. 94–98 (Sep. 1992).

Heilbrun, M. P. Progressive Technology Applications, Neurosurgery for the Third Millenium, Chapter 15, pp. 191–198 (Oct. 1992).

Henderson, J. M., et al., An Accurate and Ergonomic Method of Registration for Image–Guided Neurosurgery, Computerized Medical Imaging and Graphics, vol. 18, No. 4, pp. 273–277 (1994).

Hoerenz, P., The Operating Microscope I. Optical Principles, Illumination Systems, and Support Systems, Journal of Microsurgery, vol. 1, pp. 364–369 (1980).

Hofstetter, R. et al., Fluoroscopy Based Surgical Navigation—Concept and Clinical Applications, Computer–Assisted Radiology and Surgery, pp. 956–960 (1997).

Hounsfield, G. N., Computerized Transverse Axial Scanning (Tomography): Part I. Description of System, British Journal of Radiology, vol. 46, No. 552, pp. 1016–1022 (Dec. 1973).

Jacques, S., et al., A Computerized Microstereotactic Method to Approach, 3–Dimensionally Reconstruct, Remove and Adjuvantly Treat Small CNS Lesions, Meeting of the Amer. Soc. Stereotactic and Functional Neurosurgery, Houston, Appl. Neurophysiology, 43:176–182 (1980).

Jacques, S., et al., Computerized Three–Dimensional Stereotaxic Removal of Small Central Nervous System Lesions in Patients, J. Neurosurg., 53:816–820 (1980).

Joskowicz, L. et al., Computer–Aided Image–Guided Bone Fracture Surgery: Concept and Implementation, CAR '98, pp. 710–715.

Kelly, P. J., et al., Precision Resection of Intra–Axial CNS Lesions by CT–Based Stereotactic Craniotomy and Computer Monitored $CO_2$ Laser, Acta Neurochirurgica 68, pp. 1–9 (1983).

Lavallee, S. et al, Computer–Assisted Spine Surgery: A Technique for Accurate Transpedicular Screw Fixation Using CT Data and a 3–D Optical Localizer, pp. 315–322 (1995).

Lavallee, S., A New System for Computer–Assisted Neurosurgery, IEEE Engineering in Medicine & Biology Society 11.sup.th Annual International Conference, pp. 926–927 (1989).

Lavallee, S., et al. Computer–Assisted Interventionist Imaging: The Instance of Stereotactic Brain Surgery, North–Holland MEDINFO 89, Part 1, pp. 613–617 (1989).

Lavallee, S., et al., Computer–Assisted Driving of a Needle into the Brain, Proceedings of the International Symposium, CAR 89, Computer–Assisted Radiology; pp. 416–420 (1989).

Lavallee, S., et al., Image Guided Operating Robot: A Clinical Application in Stereotactic Neurosurgery, Proceedings of the 1992 IEEE International Conference on Robotics and Automation, pp. 618–624 (May 1992).

Lavallee, S., et al., Matching 3–D Smooth Surfaces with Their 2–D Projections Using 3–D Distance Maps, SPIE, vol. 1570, Genometric Methods in Computer Vision, pp. 322–336 (1991).

Lavallee, S., et al., Matching of Medical Images for Computed and Robot–Assisted Surgery, IEEE EMBS (1991).

Lavallee, S., VI Adaption de la Methodologie a Quelques Applications Cliniques, Chapitre VI, pp. 133–148.

Leavitt, D. et al., Dynamic Field Shaping to Optimize Stereotactic Radiosurgery, International Journal of Radiation Oncology, Biology, Physics, vol. 21, pp. 1247–1255 (Oct. 1990).

Leksell, L. et al., Stereotaxis and Tomography—A Technical Note, ACTA Neurochirugica, vol. 52, pp. 1–7 (1980).

Lemieux, L. et al., A Patient–to–Computed Tomography Image Registration Method Based on Digitally Reconstructed Radiographs, Med. Phys. 21 (11), pp. 1749–1760 (Nov. 1994).

Levin, D. N., et al., The Brain: Integrated Three–dimensional Display of MR and PET Images, Radiology, pp. 172:783–789 (Sep. 1989).

Mazier, B., et al., Chirurgie de la Colonne Vertebrale Assistee Par Ordinateur: Application au Vissage Pediculaire, Innov. Tech. Biol. Med., vol. 11, No. 5, pp. 559–566 (1990).

Mazier, B., et al., Computer–Assisted Interventionist Imaging: Application to the Vertebral Column Surgery, Annual International Conference of the IEEE Engineering in Medicine and Biology Society, vol. 12, No. 1, pp. 430–431 (1990).

Mundinger, F. et al., Computer–Assisted Stereotactic Brain Operations by Means Including Computerized Axial Tomography, Applied Neurophysiology, vol. 41, No. 1–4, Proceedings of the Seventh Meeting of the World Society for Stereotactic and Functional Neurosurgery (1978).

Pelizzari, C. A. et al., No. 528—Three–Dimensional Correlation of PET, CT and MRI Images, The Journal of Nuclear Medicine, vol. 28, No. 4, p. 682 (Apr. 1987).

Pelizzari, C. A., et al., Accurate Three–Dimensional Registration of CT, PET, and/or MR Images of the Brain, Journal of Computer–Assisted Tomography, vol. 13, No. 1, pp. 20–26 (Jan./Feb. 1989).

Perry, J. et al., Computed Tomography—Guided Stereotactic Surgery: Conception and Development of a New Stereotactic Methodology, Neurosurgery, vol. 7, No. 4, pp. 376–381 (Oct. 1980).

Phillips, R. et al., Image Guided Orthopaedic Surgery Design and Analysis, Trans Inst MC, vol. 17, No. 5, pp. 251–264 (1995).

Potamianos, P. et al., Manipulator Assisted Renal Treatment, Centre for Robotics, Imperial College of Science, Technology & Medicine, London, pp. 214–226 (Jul. 1993).

Potamianos, P., et al., Intra–Operative Imaging Guidance for Keyhole Surgery Methodology and Calibration, First International Symposium on Medical Robotics and Computer–Assisted Surgery, pp. 98–104 (Sep. 22–24, 1994).

Potamianos, P., et al., Intra–Operative Registration for Percutaneous Surgery, Proceedings of the Second International Symposium on Medical Robotics and Computer–Assisted Surgery—Baltimore, MD—(Nov. 1995).

Reinhardt, H. F., et al., CT–Guided "Real Time" Stereotaxy, ACTA Neurochirurgica (1989).

Roberts, D. W., et al., A Frameless Stereotaxic Integration of Computerized Tomographic Imaging and the Operating Microscope, J. Neurosurg., vol. 65, pp. 545–549 (Oct. 1986).

Rosenbaum, A. E., et al., Computerized Tomography Guided Stereotaxis: A New Approach, Meeting of the Amer. Soc. Stereotactic and Functional Neurosurgery, Houston, Appl. Neurophysiol., 43:172–173 (1980).

Rougee, A., et al., Geometrical Calibration of X–Ray Imaging Chains For Three–Dimensional Reconstruction, Computerized Medical Imaging and Graphics, vol. 17, Nos. 4/5, pp. 295–300 (1993).

Sautot, Pascal Phillipe, Computer Assisted Introduction of Screws Into Pedicles, Thesis, pp. 1–163 (Sep. 1994).

Schreiner, S., et al., Accuracy Assessment of a Clinical Biplane Fluoroscope for Three–Dimensional Measurements and Targeting, Proceedings of SPIE, Image Display, vol. 3031, pp. 160–166 (Feb. 23–25, 1997).

Schueler, B., Correction of Image Intensifier Distortion for Three–Dimensional X–ray Angiography, Proceedings of SPIE, Physics of Medical Imaging, vol. 2432, pp. 272–279 (Feb. 26–27, 1995).

Selvik, G., et al., A Roentgen Stereophotogrammetric System, Acta Radiologica Diagnosis, pp. 343–352 (1983).

Shelden, C. H., et al., Development of a Computerized Microstereotaxic Method for Localization and Removal of Minute CNS Lesions Under Direct 3–D Vision, J. Neurosurg., 52:21–27 (1980).

Simon, D., Fast and Accurate Shape–Based Registration, Carnegie Mello University (Dec. 12, 1996).

Smith, K. et al., The Neurostation.TM.—A Highly Accurate, Minimally Invasive Solution to Frameless Stereotactic Neurosurgery, Computerized Medical Imaging and Graphics, vol. 18, No. 4, pp. 247–256 (Jul.–Aug. 1994).

Smith, K. R., et al., Computer Methods for Improved Diagnostic Image Display Applied to Stereotactic Neurosurgery, Automedical, vol. 14, pp. 371–386 (1991).

Troccaz, J. et al., Conformal External Radiotherapy of Prostatic Carcinoma: Requirements and Experimental Results, Radiotherapy and Oncology 29, pp. 176–183 (1993).

Viant, W. J. et al., A Computer–Assisted Orthopaedic System for Distal Locking of Intramedullary Nails, Proc. of MediMEC '95, Bristol, pp. 86–91 (1995).

Watanable, E., et al., Three–Dimensional Digitizer (Neuronavigator): New Equipment for Computed Tomography–Guided Stereotaxic Surgery, Surgical Neurology, vol. 27, No. 6, pp. 543–547 (Jun. 1987).

Watanabe, H., Neuronavigator, Igaku–no–Ayumi, vol. 137, No. 6, pp. 1–4 (May 10, 1986).

Weese, J., et al., An Approach to 2D/3D Registration of a Vertebra in 2D X–ray Fluoroscopies with 3D CT Images, First Joint Conference Computer Vision, Virtual Reality and Robotics in Medicine and Med. Robotics and Computer–Assisted Surgery, Grenoble, France, pp. 119–128 (Mar. 19–22, 1997).

"Prestige Cervical Disc System Surgical Technique", 12 pgs.

Adams et al., "Orientation Aid for Head and Neck Surgeons," Innov. Tech. Biol. Med., Vol. 13, No. 4, 1992, pp. 409–424.

Benzel et al., "Magnetic Source Imaging: a Review of the Magnes System of Biomagnetic Technologies Incorporated," Neurosurgery, vol. 33, No. 2 (Aug. 1993), pp. 252–259.

Bryan, "Bryan Cervical Disc System Single Level Surgical Technique", Spinal Dynamics, 2002, pp. 1–33.

Heilbrun et al., "Preliminary experience with Brown–Roberts–Wells (BRW) computerized tomography stereotaxic guidance system," Journal of Neurosurgery, vol. 59, Aug. 1983, pp. 217–222.

Horner et al., "A Comparison of CT–Stereotaxic Brain Biopsy Techniques," Investigative Radiology, Sep.–Oct. 1984, pp. 367–373.

Kelly et al., "Computer–assisted stereotaxic laser resection of intra–axial brain neoplasms," Journal of Neurosurgery, vol. 64, Mar. 1986, pp. 427–439.

Laitinen et al., "An Adapter for Computed Tomography–Guided, Stereotaxis," Surg. Neurol., 1985, pp. 559–566.

Laitinen, "Noninvasive multipurpose stereoadapter," Neurological Research, Jun. 1987, pp. 137–141.

Pelizzari et al., "Interactive 3D Patient–Image Registration," Information Processing in Medical Imaging, 12th International Conference, IPMI '91, Jul. 7–12, 136–141 (A.C.F. Colchester et al. eds. 1991).

Sautot, "Vissage Pediculaire Assiste Par Ordinateur," Sep. 20, 1994.

Smith et al., "The Neurostation™—A Highly Accurate, Minimally Invasive Solution to Frameless Stereotactic Neurosurgery," Computerized Medical Imaging and Graphics, vol. 18, Jul.–Aug., 1994, pp. 247–256.

The Laitinen Stereotactic System, E2–E6.

Germano, "Instrumentation, Technique and Technology", Neurosurgery, vol. 37, No. 2, Aug., 1995, pp. 348–350.

Merloz, et al., "Computer Assisted Spine Surgery", Clinical Assisted Spine Surgery, No. 337, pp. 86–96.

Hatch, et al., "Reference–Display System for the Integration of CT Scanning and the Operating Microscope", Proceedings of the Eleventh Annual Northeast Bioengineering Conference, May, 1985, pp. 252–254.

* cited by examiner

METHOD AND APPARATUS FOR VIRTUAL DIGITAL SUBTRACTION ANGIOGRAPHY

FIELD OF THE INVENTION

The present invention relates generally to medical imaging systems and, more particularly, to a system that detects any change in relative position between a patient and the imaging device and corrects the image data for any such motion that occurs.

BACKGROUND OF THE INVENTION

Modern diagnostic medicine has benefited significantly from radiology. Radiation, such as x-rays, may be used to generate images of internal body structures. In general, radiation is emanated towards a patient's body and absorbed in varying amounts by tissues in the body. An x-ray image is then created based on the relative differences of detected radiation passing through the patients' body.

Digital subtraction is a well known technique for visually enhancing differences between such images. For example, digital subtraction angiography (DSA) is used to visualize vasculature by comparing two or more images of the same blood vessels before and after injection of a contrast agent. Assuming that the only change between the pre-contrast image (or "mask") and the contrast-containing image is related to the injection of the contrast agent, the "difference image" clearly outlines the vessels into which the contrast agent has flowed.

However, digital subtraction techniques assume a fixed relative position between the imaging device and the patient being imaged for any images which are being compared. If this relative position changes between the time that the initial image (the one to which all subsequent images are compared) is acquired and the time that any of the subsequent images are acquired, the difference image will not only convey changes in the anatomy of the patient, but also any "artifacts" or changes introduced by this change in relative position between the imaging device and the patient.

Therefore, it is desirable to provide a medical imaging system that addresses the patient motion artifact problem. It is envisioned that the system will directly measure the relative position between the imaging device and the patient, and then compensate the images for any motion that occurs between the time at which the initial image is acquired and the time at which any subsequent images are acquired by the imaging system.

SUMMARY OF THE INVENTION

In accordance with the present invention, a medical imaging system is provided that detects any change in relative position between the patient and the imaging device and compensates the image data for any patient motion that occurs. The medical imaging system includes: an imaging device for capturing two or more image data sets representative of a patient; a tracking subsystem for detecting patient position data that is indicative of the position of the patient and device position data that is indicative of the position of the imaging device; an image subtraction subsystem for performing a digital subtraction operation between at least two image data sets; and a motion correction subsystem configured to detect a change in the relative position between the patient and the imaging device and upon detecting a change in the relative position, compensate in at least one of the first image data set and the second image data set for the change in relative position prior to performing the digital subtraction operation. The digital subtraction image can detect the motion of a therapeutic device, motion of a therapy as it moves through the body, perfusion of a substance, contrast agents, chemical change of a substance, a drug as it attaches itself to anatomical material or interacts with diseased tissue, or any device or substance that has an image signature within one or multiple image modalities. The digital subtraction of any 3D volume such as those created by MR, CT, Isocentric C-arms, C-arms tracked to construct volumes, 3D ultrasound, etc. can now be viewed from any angle or with any cut plane. It is also important to point out that the tracking subsystem can be implemented via a number of different devices or techniques in order to correct for patient motion. Simple modeling of patient respiration or heart cycles can be used in conjunction with a tracking subsystem or solely to provide motion correction. The system could use actual signals as inputs to these models.

For a more complete understanding of the invention, reference may be had to the following specification and to the accompanying drawings.

DETAILED DESCRIPTION OF THE PREFERRED EMBODIMENTS

Figure 1:
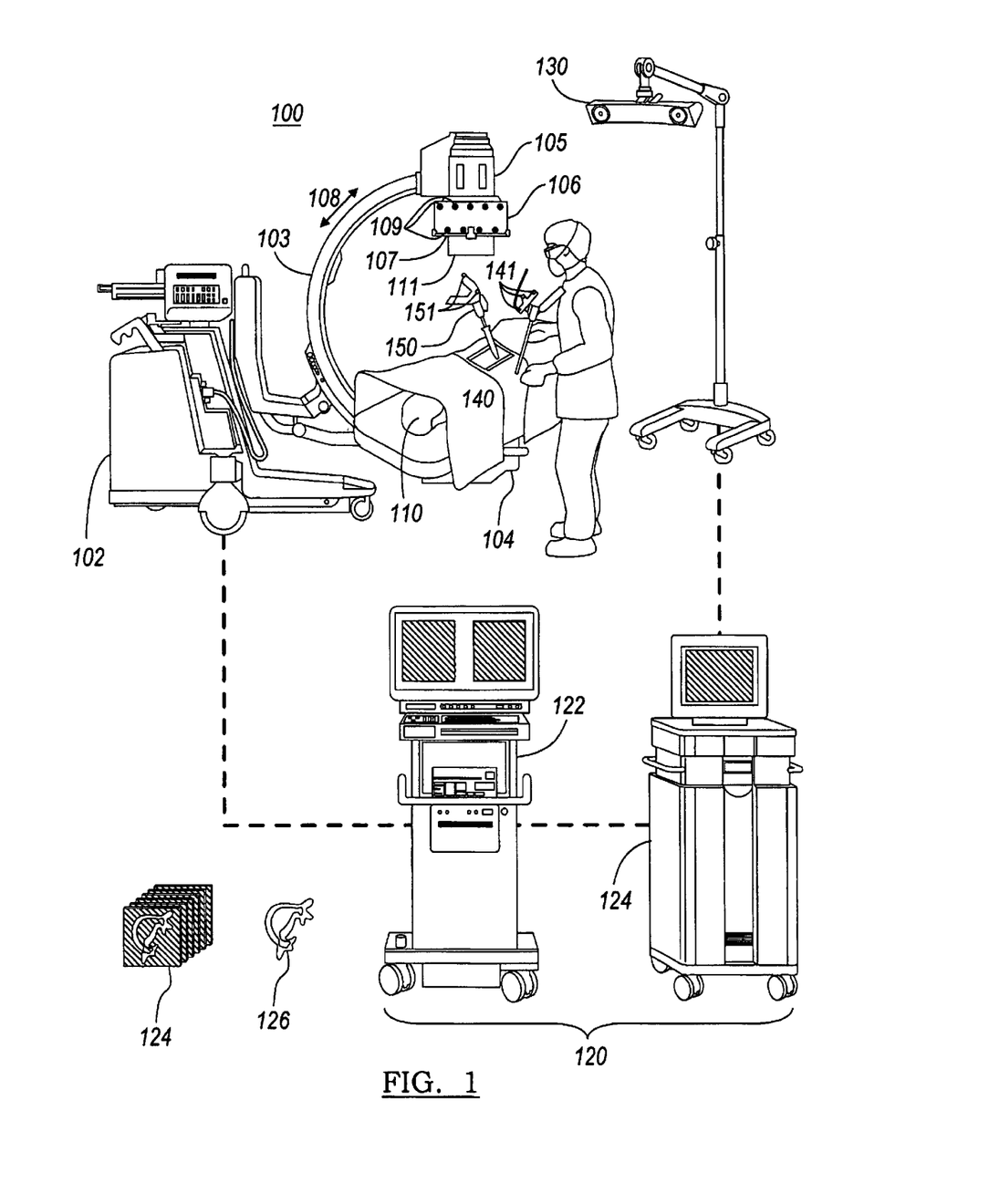
FIG. 1 is a diagram of a surgical instrument navigation system in accordance with present invention.

FIG. 1 is a diagram of an exemplary surgical instrument navigation system. The primary component of the surgical instrument navigation system is a fluoroscopic imaging device 100. The fluoroscopic imaging device 100 generally includes a C-arm 103 attached to a mobile base 102 or fixed room system. An x-ray source 104 is located at one end of the C-arm 103 and an x-ray receiving section 105 is located at the other end of the C-arm 103. In addition, the fluoroscopic imaging device 100 includes a calibration and tracking target 106 attached to the x-ray receiving section 105. As will be further described below, the calibration and tracking target 106 further includes one or more radiation sensors 107, a plurality of tracking targets 109, and a plurality of calibration markers 111. While the following description is provided by reference to an x-ray imaging device, it is readily understood that other types on imaging devices, such as a computed tomography imaging device, a magnetic resonance imaging device or an ultra-sound device, are within the scope of the present invention. It is also readily understood that two-dimensional projection images or three-dimensional volumetric images are within the scope of the present invention.

In operation, a patient 110 is positioned between the x-ray source 104 and the x-ray receiving section 105. In response to an operator's command input, x-rays emanating from source 104 pass through the patient area, including the patient 110 and the calibration and tracking target 106, and into the receiving section 105 of the imaging device. The receiving section 105 generates a two-dimensional image based on the intensities of the received x-rays. To do so, the receiving section 105 may be comprised an image intensifier that converts the x-rays to visible light and a charge coupled device (CCD) video camera that converts the visible light to digital images. Alternatively, the receiving section 105 may be a device that converts x-rays directly to digital images, thus potentially avoiding distortion introduced by first converting to visible light.

Furthermore, the C-arm 103 is capable of rotating relative to the patient 110, thereby allowing images of the patient 110 to be taken from multiple directions. For example, the physician may rotate the C-arm 103 in the direction of arrows 108 or about the long axis of the patient 110. Each of these directions of movement involves rotation about a mechanical axis of the C-arm 103. In this example, the long axis of the patient 110 is aligned with the mechanical axis of the C-arm 103. In sum, the imaging device 100 is generally operable to capture one or more sets of image data representative of the patient 110.

Resulting fluoroscopic images are then transmitted to an image processing device 120. In one embodiment, the image processing device 120 may be comprised of two computers. A control computer 122 which allows a physician to control the fundamental operation of the imaging device 100, such as setting imaging parameters, and a second computer 124 which may be used to perform more robust image processing functions. It is envisioned that either computer may provide facilities for displaying, saving, digitally manipulating, or printing a hard copy of the received images. It is further envisioned that images may be displayed to the physician through a heads-up display (not shown). It is readily understood that these computing functions may be integrated into a single computer or distributed across three or more computing devices.

An exemplary imaging device 100 is the Series 9800 Mobile Digital Imaging System manufactured by OEC Medical Systems, Inc. of Salt Lake City, Utah. It should be noted that calibration and tracking target 106 is typically not included in the Series 9800 Mobile Digital Imaging System, but otherwise this system is similar to the imaging system 100 described above. An alternative imaging device is the SIREMOBILE Iso-C System manufactured by Siemens Medical Systems, Inc. of Iselin, N.J.

Figure 2:
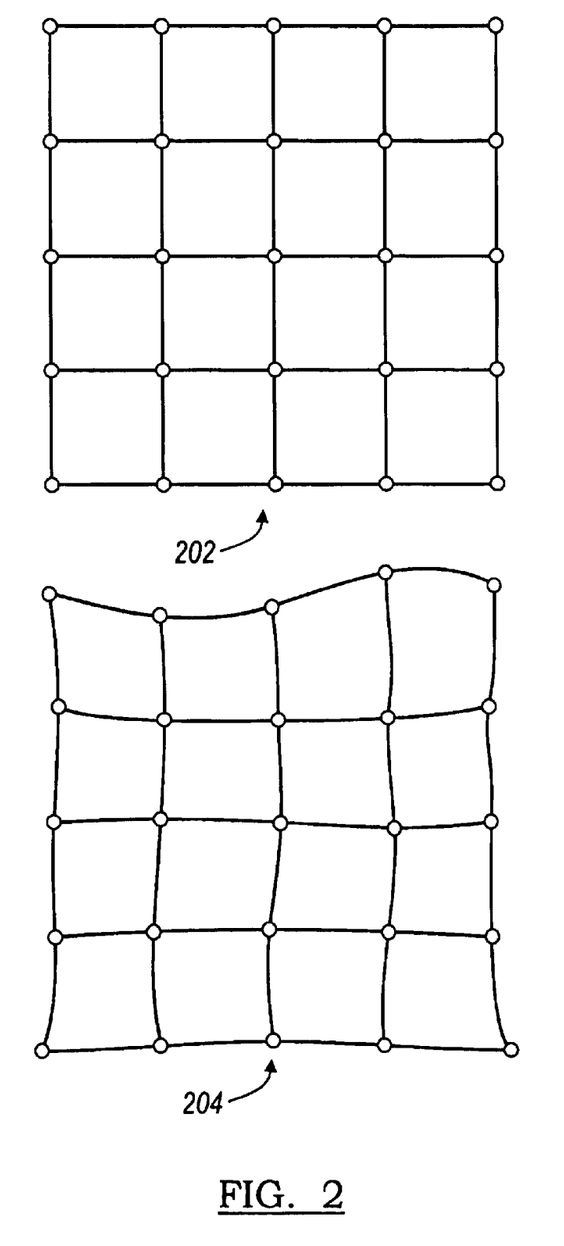
FIG. 2 is a diagram of a true and a distorted image that may be captured by the surgical navigation system.

Intrinsic calibration is the process of correcting image distortion in a received image and establishing the projective transformation for that image. Raw images generated by the receiving section 105 tend to suffer from undesirable distortion caused by a number of factors, including inherent image distortion in the image intensifier and external electromagnetic fields. An example of a true and a distorted image is shown in FIG. 2. Checkerboard 202 represents the true image of a checkerboard shaped object placed in the image tracking area. The image taken by receiving section 105, however, can suffer significant distortion, as illustrated by the distorted image 204.

Figure 3A:
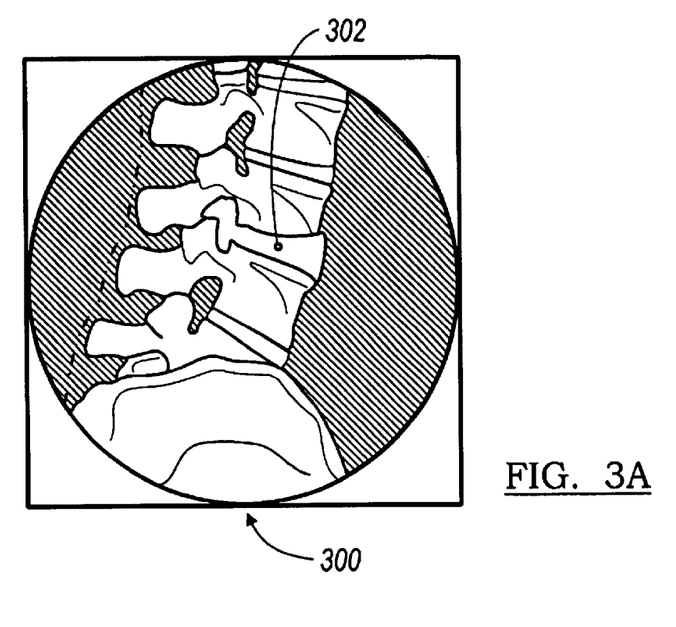
FIGS. 3A and 3B illustrates the projective transformation process employed by the surgical navigation system.
Figure 3B:
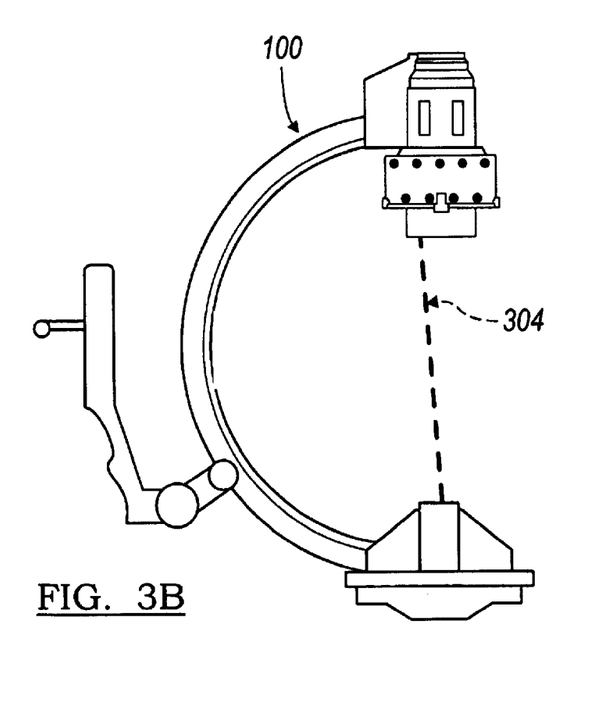

Furthermore, the image formation process is governed by a geometric projective transformation which maps lines in the fluoroscope's field of view to points in the image (i.e., within the x-ray receiving section 105). This concept is illustrated in FIGS. 3A and 3B. Image 300 (and any image generated by the fluoroscope) is composed of discrete picture elements (pixels), an example of which is labeled as 302. Every pixel within the image 300 has a corresponding three-dimensional line in the fluoroscope's field of view. For example, the line corresponding to pixel 302 is labeled as 304. The complete mapping between image pixels 302 and corresponding lines 304 governs projection of objects within the field of view into the image. The intensity value at pixel 302 is determined by the densities of the object elements (i.e., portions of a patient's anatomy, operating room table, etc.) intersected by the line 304. For the purpose of computer assisted navigational guidance, it is necessary to estimate the projective transformation which maps lines in the field of view to pixels in the image, and vice versa.

Intrinsic calibration involves placing "calibration markers" in the path of the x-ray, where a calibration marker is an object opaque or semi-opaque to x-rays. Calibration markers 111 are rigidly arranged in predetermined patterns in one or more planes in the path of the x-rays and are visible in the recorded images. Because the true relative position of the calibration markers 111 in the recorded images are known, the image processing device 120 is able to calculate an amount of distortion at each pixel 302 in the image (where a pixel is a single point in the image). Accordingly, the image processing device 120 can digitally compensate for the distortion in the image and generate a distortion-free, or at least a distortion improved image. Alternatively, distortion may be left in the image, and subsequent operations on the image, such as superimposing an iconic representation of a surgical instrument on the image (described in more detail below), may be distorted to match the image distortion determined by the calibration markers.

Since the position of the calibration markers 111 are known with respect to the tracking targets 109 and ultimately with respect to a tracking sensor, the calibration markers 111 can also be used to estimate the geometric perspective transformation. A more detailed explanation of methods for performing intrinsic calibration is described in the following references B. Schuele et al., "Correction of Image Intensifier Distortion for Three-Dimensional Reconstruction," presented at SPIE Medical Imaging 1995, San Diego, Calif., 1995 and G. Champleboux et al., "Accurate Calibration of Cameras and Range Imaging Sensors: the NPBS Method," Proceedings of the 1992 IEEE International Conference on Robotics and Automation, Nice, France, May 1992, and U.S. Pat. No. 6,118,845, issued Sep. 12, 2000 by the present assignee, the contents of which are hereby incorporated by reference.

The surgical instrument navigation system further includes a tracking subsystem. The tracking subsystem is generally comprised of a non-contact position location sensor, numerous tracking targets embedded in different system components and accompanying computational software implemented in the image processing device 120. In a preferred embodiment, the tracking subsystem employs a real-time infrared tracking sensor 130. Although an infrared-based tracking subsystem (either passive or active) is presently preferred, it is envisioned that other well known types of positional location devices may be used to implement the tracking subsystem. For example, positional location devices based on mechanical arms, robotics, radio wave, magnetic fields, fiber optic, or sonic emissions are also within the scope of the present invention.

The tracking sensor 130 detects the presence and location of a surgical instrument 140. To do so, the specially constructed surgical instrument 140 is embedded with tracking targets 141, such as infrared reflectors or emitters. Because the relative spatial locations of the tracking targets 141 on the surgical instrument 140 are known a priori, the tracking subsystem is able to determine the location of the surgical instrument 140 in three-dimensional space using well known mathematical transformations.

During an operation, a dynamic reference frame marker 150 is attached in a fixed position relative to the portion of the patient 110 to be operated on. For example, when inserting a screw into the spine of the patient 110, the dynamic reference frame marker 150 may be physically attached to a portion of the spine of the patient 110. The reference frame marker 150 is similarly embedded with tracking targets 151, such as infrared reflectors or emitters. In this way, the tracking sensor 130 is also able to determine the location of reference frame marker 150 in three-dimensional space.

Consequently, the surgical instrument 140 can be accurately located in three dimensional space relative to the reference frame marker 150 and thus can be located relative to the patient's anatomy. The determination of the three-dimensional position of an object, such as the reference frame marker, relative to a patient is known in the art, and is discussed, for example, in the following references, each of which are hereby incorporated by reference: PCT Publication WO 96/11624 to Bucholz et al., published Apr. 25, 1996; U.S. Pat. No. 5,384,454 to Bucholz; U.S. Pat. No. 5,851,183 to Bucholz; and U.S. Pat. No. 5,871,445 to Bucholz.

Lastly, the calibration and tracking target 106 also includes tracking targets 109, such as infrared reflectors or emitters. In a similar manner, the tracking sensor 130 detects the presence and location of the tracking targets 109. Since the calibration and tracking target 106 is in a fixed position relative to the x-ray receiving section 105, the image processing device 120 can further determine the three-dimensional position of the x-ray receiving section 105 relative to the surgical instrument 140 and/or the dynamic reference frame 150 (and thus the patient).

In one embodiment, the tracking sensor 130 determines the position of the x-ray receiving section 105 at each point in time that it captures image data. In an alternative embodiment, position data for the x-ray receiving section 105 is reported by a mechanical localizer associated with the imaging device 100. The mechanical localizer is operable to report position data for the x-ray receiving section 105 relative to a baseline position. In operation, the tracking sensor 130 may be used to determine the baseline position of the x-ray receiving section 105 relative to the either the surgical instrument 140 and/or the dynamic reference frame 150. Alternatively, you may simply touch the surgical instrument 140 to various reference points on the x-ray receiving section 105. Thereafter, as position of the x-ray receiving section 105 changes over time, its position is reported by the mechanical localizer. In other words, by first determining the baseline location, subsequent movement and location of imaging device 100 can be determined by monitoring the drive or movement mechanism surgical localizer of the imaging device 100. The image processing device 120 can then determine the position of the x-ray receiving device 105 relative to either the surgical instrument 140 and/or the dynamic reference frame 150.

In operation, the enhanced surgical navigation system assists physicians performing surgery by displaying real-time or pre-acquired images, such as fluoroscopic x-ray images, of the patient 110 on a display associated with image processing device 120 that is visible to the surgeon. Representations of surgical instruments 140 are overlaid on pre-acquired fluoroscopic images of the patient 110 based on the position of the instruments 140 as determined by the tracking sensor 130. In this manner, the surgeon is able to see the location of the instrument 140 relative to the patient's anatomy, without the need to acquire real-time fluoroscopic images, thereby greatly reducing radiation exposure to the patient and to the surgical team.

Figure 4:
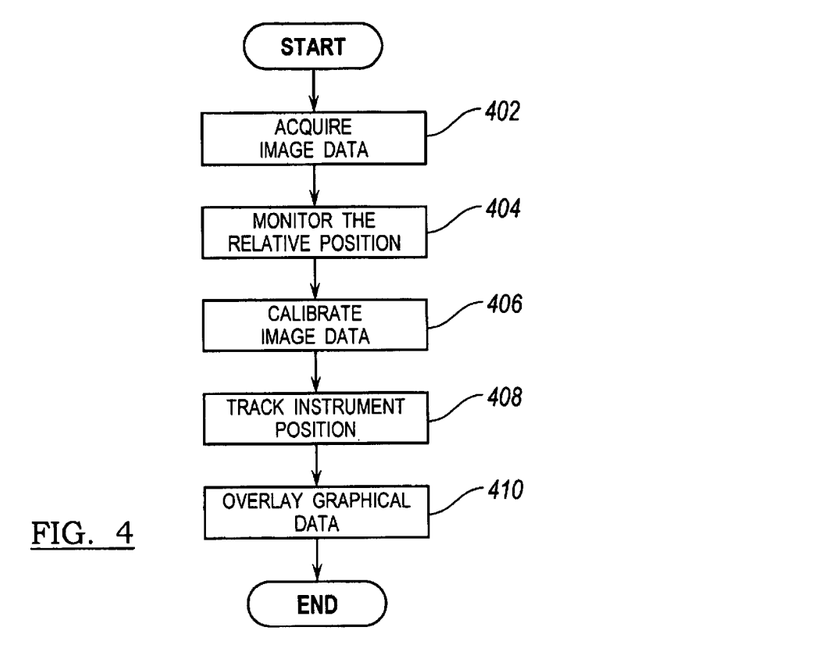
FIG. 4 is a flowchart depicting the operation of the enhanced surgical navigation system of the present invention.

FIG. 4 is a flowchart depicting the operation of the surgical navigation system. The physician begins by acquiring one or more fluoroscopic x-ray images of the patient 110 using the imaging device 100 as shown at 402. Radiation sensors 107 embedded in the calibration and tracking target 106 may be used to detect the presence of radiation. The image processing device 120 uses input from the radiation sensors 107 to determine the beginning and end of a radiation cycle. Alternatively, the operator may manually indicate the beginning and end of a radiation cycle or a signal may be sent from the imaging device.

For a fluoroscopic x-ray image to be useable for navigational guidance, the imaging device 100 must be stationary with respect to the patient 110 during image acquisition. If the C-arm 103 or the patient 110 is moving during image acquisition, the position of the imaging device will not be accurately determined relative to the patient's reference frame. Thus, it is important that the recorded position of imaging device 100 reflects its true position at the time of image acquisition.

During the image acquisition process, the image processing device 120 continuously examines the relative position between the patient 110 and the imaging device 100 as shown at 404. If the imaging device 100 moves during the image acquisition process, or if the imaging device 100 moves after image acquisition but before its position is recorded, calibration measurements will be erroneous, thereby resulting in incorrect graphical overlays. To prevent this type of erroneous image, image data may be discarded if the patient 110 moves relative to the imaging device 100 during the image acquisition process.

At the end of the radiation cycle, the image processing device 120 retrieves the acquired image data as well as positional data for the imaging device 100 and the dynamic reference frame 150. The image processing device 120 subsequently calibrates the acquired image to learn its projective transformation and optionally to correct distortion in the image at 406. Calibrated image data along with corresponding positional data is then stored. These processing steps are repeated for each image that is acquired.

During surgery, the tracking sensor 130 detects the position of surgical instrument 140 relative to the dynamic reference frame 150, and hence relative to the patient 110 at 408. The image processing device 120 dynamically computes, in real-time, the projection of instrument 140 into each fluoroscopic image as the instrument 140 is moved by the physician. A graphical representation of instrument 140 may then be overlaid on the fluoroscopic images at 410. The graphical representation of instrument 140 is an iconic representation of where the actual surgical instrument 140 would appear within the acquired fluoroscopic x-ray image as if the imaging device 100 was continuously acquiring new images from the same view as the original image. There is no theoretical limit to the number of fluoroscopic images on which the graphical representations of instrument may be simultaneously overlaid.

Figure 5:
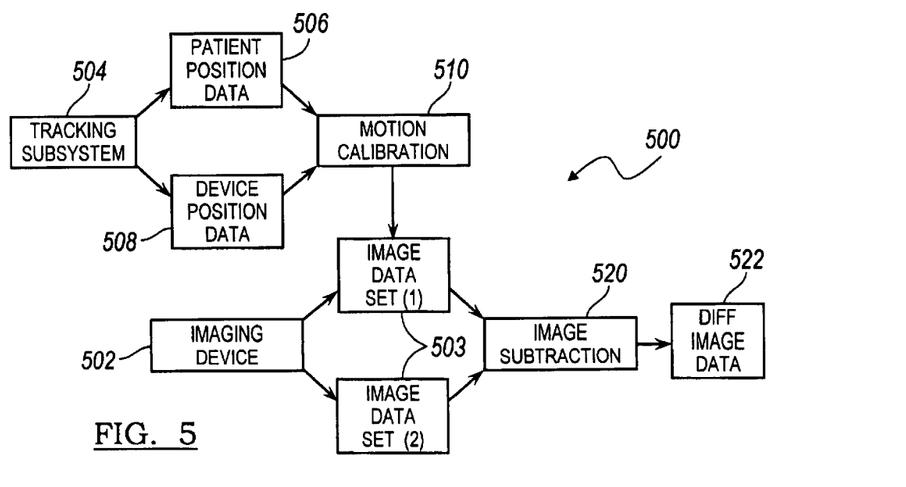
FIG. 5 is a block diagram of an enhanced surgical instrument navigation system in accordance with the present invention.

In accordance with the present invention, the surgical instrument navigation system described above has been enhanced to detect any change in relative position between the patient 110 and the imaging device 100, and compensate image data for any such patient motion. Referring to FIG. 5, the enhanced surgical navigation system 500 includes an imaging device 502 and a tracking subsystem 504. As described above, the imaging device 502 is operable to capture one or more image data sets representative of a patient; whereas the tracking subsystem 504 is operable to determine patient position data 506 indicative of the position of the patient as well as device position data 508 indicative of the position of the imaging device.

The enhanced surgical instrument navigation system 500 further includes a motion correction subsystem 510 and an image subtraction subsystem 520. The image subtraction subsystem 520 is adapted to receive two image data sets 503 from the imaging device 502. The image subtraction subsystem 520 is then operable to perform a digital subtraction operation between the two image data sets, thereby generating resulting image data 522 indicative of the differences between the two image data sets. Further explanation of exemplary digital subtraction techniques is described in Christensen's Physics of Diagnostic Radiology by Thomas S. Curry, III, James E. Dowdey, and Robert C. Murry, Jr., $4^{th}$ Ed. 1990, the contents of which are hereby incorporated by reference. It is readily understood that various well known digital subtraction techniques are within the scope of the present invention. It is further understood that other comparison techniques for assessing image data acquired at different points in time are also within the scope of the present invention. Any sort of image analysis or comparison can be applied to such a technique as segmentation, volume rendering, or shape analysis to a brain structure such as the hippocampus or tumor growth. One such technique for shape analysis is described in U.S. patent application Ser. No. 09/326,657 Method and Apparatus for Automatic Shape Characterization and U.S. Pat. No. 6,226,418 which are specifications are here included.

Figure 7:
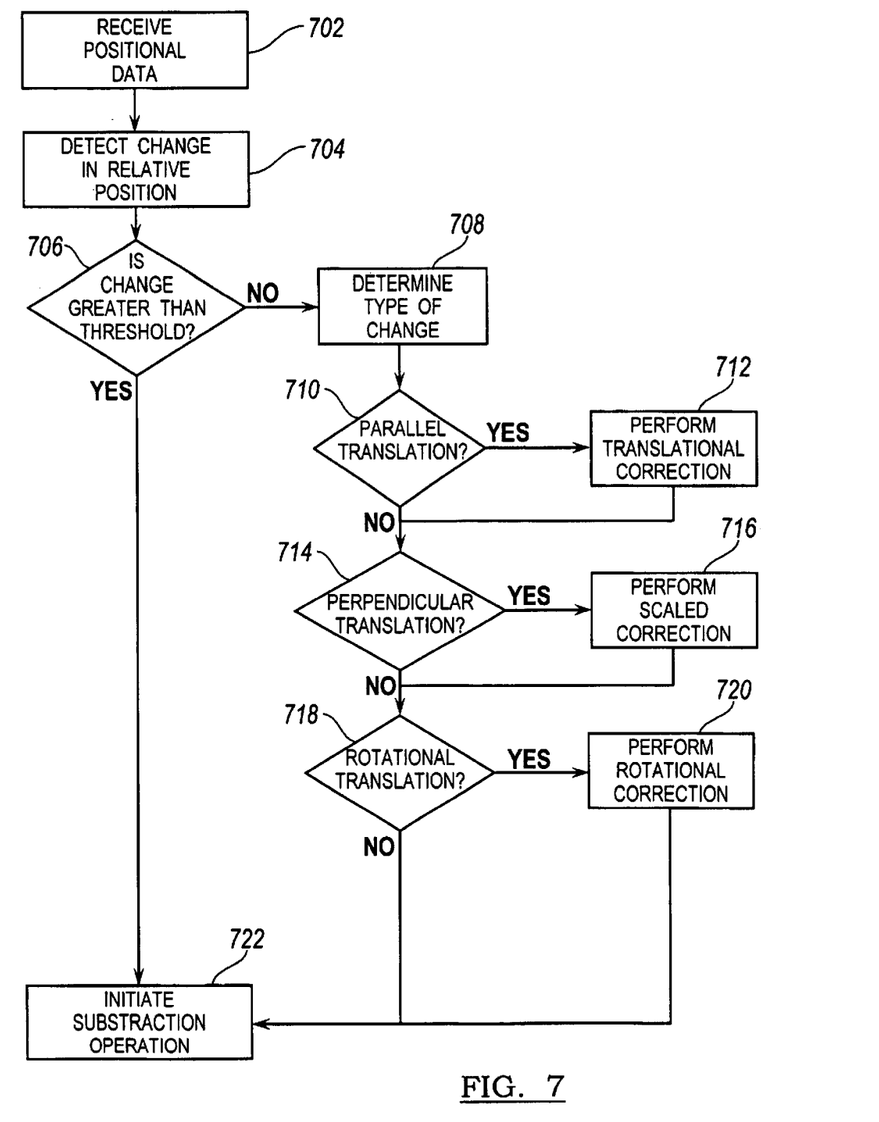
FIG. 7 is a flowchart depicting the operation of the motion correction subsystem in accordance with the present invention.

Prior to performing a digital subtraction operation, the motion correction subsystem 510 may be used to detect any patient motion that occurs between the times at which the image data is acquired. Referring to FIG. 7, the motion correction subsystem 510 is adapted to receive the patient position data 506 and device position data 508 corresponding to each of the two image data sets 503 as shown at 702. The motion correction subsystem 510 is then operable to detect any change in the relative position between the patient and the imaging device as shown at 704.

In one embodiment, the detection of patient motion merely serves as a triggering event for the operation of the enhanced surgical navigation system 500. When no change occurs in the relative position of the patient, a digital subtraction operation may simply be performed by the image subtraction subsystem 520. Alternatively, the digital subtraction operation may be performed when the measured change in relative position is less than a predetermined threshold value that is indicative of a maximum acceptable change in the relative position between the patient and the imaging device. On the other hand, when a unacceptable amount of patient motion is detected, the motion correction subsystem 510 may initiate an alternate operation, such as providing an operator alarm.

In another embodiment, the motion correction subsystem 510 may measure the change in relative position between the patient and the imaging device over time. When the measured change in relative position is less than the predetermined threshold value, the motion correction subsystem 510 initiates the digital subtraction operation at 722. On the other hand, when the measured change in relative position is equal to or greater than the predetermined threshold value, the motion correction subsystem 510 will apply a suitable correction to at least one of the two image data sets.

Figure 6A:
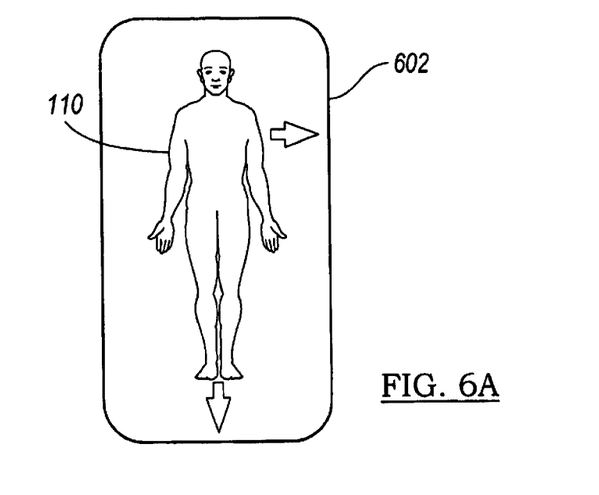
FIGS. 6A–6C illustrates the different types of changes in the relative position between the patient and the imaging device.
Figure 6B:
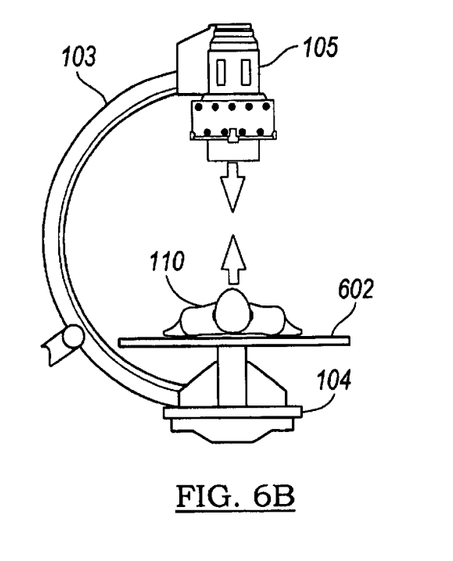

Since the suitable correction depends upon the nature of the relative motion, the motion correction subsystem 501 is operable to determine the nature of the relative motion at 708. For instance, when the relative motion (or change in relative position) is a translation that is parallel to the imaging plane 602 of the imaging device, a suitable translation correction would be performed to one of the two images as shown at 712. FIG. 6A illustrates a translation that is parallel to the imaging plane 602 of the imaging device (e.g., the face of the image intensifier of a fluoroscope). When the relative motion is a translation that is perpendicular to the imaging plane 602, a change occurs in the scale or size of the imaged anatomy as shown at 716. In this case, a suitable scale correction would be performed to one of the two images. FIG. 6B illustrates a translation that is perpendicular to the imaging plane 602 of the imaging device (as represented by the top surface of operating table). Suitable image correction techniques are well known in the art.

Figure 6C:
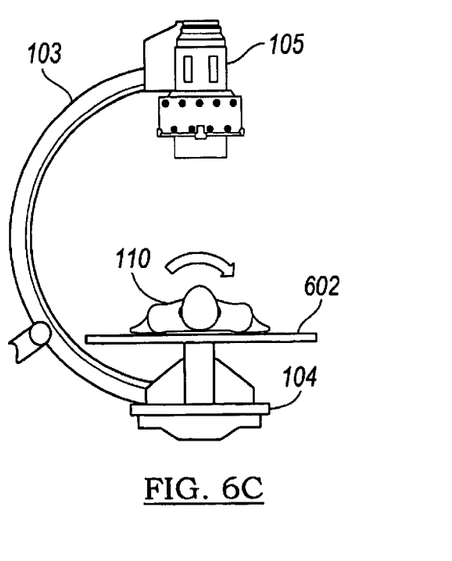

When the relative motion is a rotation of the imaging device about the patient's anatomy, the ability to perform a correction depends upon the magnitude and direction of the rotation. FIG. 6C illustrates motion that is rotational to the imaging plane 602 of the imaging device. Rotations of the imaging device relative to the anatomy in a plane parallel to the image plane can be corrected by applying an appropriate in plane rotation to one of the two images. However, in the case of two-dimensional projection imaging, it is impossible to correct for arbitrary rotations without knowing the three-dimensional shape of the underlying anatomy. In some of these cases, the rotational correction may be approximated using known translation techniques. Therefore, it is envisioned that the motion correction subsystem 510 may further include a mechanism for determining when a rotational correction can be performed by a translation and then applying an appropriate rotational translation as shown at 720. It is readily understood that in the case of three-dimensional volumetric images, the limitation on correcting for rotations does not apply, and a complete correction can be applied to the image data.

Once an appropriate correction has been applied to either of the two image data sets, the motion correction subsystem 510 initiates a digital subtraction operation at 722. It is to be understood that only the relevant steps of the methodology are shown in FIG. 7, but that other software-implemented instructions may be needed to control and manage the overall operation of the subsystem.

In two-dimensional projection imaging, determining how to apply a correction to an image given a measurement of the relative motion between patient and the imaging device requires an additional piece of information. In particular, the intrinsic calibration parameters of the imaging device must be known to the motion correction subsystem 510.

In three-dimensional digital subtraction, it is possible to compute volume changes of the contrast media as a function of time. Once the motion correction is applied, this would be computed as the volume of the difference image above a given intensity threshold. This difference volume could be further constrained to lie within a segmented region (e.g., within a vertebral body, outside a vertebral body). Computation of other shape attributes (surface area, moments of inertia, etc.) are also possible.

It is further envisioned that the motion correction subsystem 510 may be configured to eliminate motion artifacts caused by changes in the position of the tracked surgical instrument 140. Recall that any changes in the imager's field of view will result in an enhanced region of the difference image. Typically, the motion of the surgical instrument 140 is not clinically relevant and, therefore, it would be desirable to eliminate these enhanced regions from any resulting difference image. Using the measured positions of a given instrument 140 relative to the imaging device 100, together with data for the three-dimensional shape of the instrument (e.g., from a CAD model), it is possible to compute the resulting enhanced region in the difference image. Once this region is known, it is then possible to eliminate this instrument-induced motion artifact from the image. It is to be understood that this function can be applied to either two-dimensional projection images or three-dimensional volumetric images.

While the above description is provided with reference to a surgical navigation system, it is readily understood that the broader aspects of the present invention are generally applicable to medical imaging systems where motion between the patient and the imaging device is suspected.

Moreover, it is readily understood that the present invention is applicable to different types of medical applications. One medical application of interest is vertebroplasty, in which bone cement is injected into a vertebral body of the spine via a needle that passes through the spinal pedicle. Leakage of this cement into surrounding structures can result in serious complications. Therefore, visualizing the spread of this cement over time is critical so that the clinician can ensure that the cement does not leave the vertebral body. One way to achieve this goal is by using single or multi-planar fluoroscopic imaging to view the anatomical structures as the above-mentioned cement is introduced. Unfortunately, the cement is often poorly visualized in the fluoroscopic images. Digital subtraction radiology provides a mechanism for highlighting the location of the cement by comparing a pre-cement image to one or more images acquired while the cement is being injected. Unfortunately, due to the nature of the clinical procedure, there is a moderate likelihood that the spinal anatomy will move relative to the imaging device as the cement is being injected. By applying the methods and systems of the present invention, it is possible to compensate for this motion, thereby making digital subtraction techniques feasible for this application.

Another medical application may involve a comparison between vector fields computed in an area to represent brain shifts or other soft tissue deformations. Other possible medical applications may include but are not limited to monitoring the introduction of embolics into vascular aneurysms; introduction of cement into other bony anatomy; bone density analysis; etc. Analysis of bone morphogenic protein dispersion through the bone for spinal or orthopedic applications may be completed by looking at the slightest changes in bone density or other carrier with an image signature to monitor effectiveness or used to indicate or compute new dosages need to be administered. It is readily apparent from some of these examples that the time period between acquired image data may range from a few seconds to days or weeks.

While the invention has been described in its presently preferred form, it will be understood that the invention is capable of modification without departing from the spirit of the invention as set forth in the appended claims.

What is claimed is:

1. A medical imaging system, comprising:
an imaging device operable to capture two or more image data sets representative of a patient;
a tracking subsystem operable to detect patient position data corresponding to each image data set and device position data corresponding to each image data set, where the patient position data is indicative of the position of the patient and the device position data is indicative of the position of the imaging device;
a motion correction subsystem adapted to receive patient position data corresponding to the first and second image data set and device position data corresponding to the first and second image data set, and the motion correction subsystem is operable to detect a change in relative position between the patient and the imaging device; and
an image subtraction subsystem adapted to receive at least a first image data set and a second image data set from the imaging device, the image subtraction subsystem is operable to perform a digital subtraction operation between the first image data set and the second image data set when no substantial change occurs in the relative position between the patient and the imaging device.

2. The medical imaging system of claim 1 wherein the imaging device includes an image source operable to emanate radiation towards the patient and an image receiver positioned to receive radiation from the image source.

3. The medical imaging system of claim 1 wherein the imaging device is selected from the group consisting of an x-ray imaging device, a computed tomography imaging device and a magnetic resonance imaging device.

4. The medical imaging system of claim 1 wherein the tracking subsystem is further defined as an infrared tracking sensor.

5. The medical imaging system of claim 1 wherein the imaging device further includes a plurality of tracking targets that are detectable by the tracking subsystem.

6. The medical imaging system of claim 1 further comprises a reference frame marker positioned in a fixed location relative to the patient, where the reference frame marker includes tracking targets that are detectable by the tracking subsystem.

7. The medical imaging system of claim 6 wherein the reference frame marker is physically attached to a portion of the patient.

8. The medical imaging system of claim 1 wherein the motion correction subsystem is further operable to generate an operator alarm upon detection of a change in the relative position between the patient and the imaging device.

9. The medical imaging system of claim 1 further comprising a surgical instrument having tracking targets that are detectable by the tracking subsystem, such that the tracking subsystem detects in real-time instrument position data indicative of the position of the surgical instrument.

10. The medical imaging system of claim 9 wherein the motion correction subsystem is adapted to receive instrument position data from the tracking subsystem and operable to compensate for a change in the position of the surgical instrument in at least one of the first image data set and the second image data set.

11. A medical imaging system, comprising:
an imaging device operable to capture two or more image data sets representative of a patient;
a tracking subsystem operable to detect patient position data corresponding to each of the image data sets and device position data corresponding to each the image data sets, where the patient position data is indicative of the position of the patient and the device position data is indicative of the position of the imaging device;

an image subtraction subsystem adapted to receive at least a first image data set and a second image data set from the imaging device, the image subtraction subsystem operable to perform a digital subtraction operation between the first image data set and the second image data set; and a motion correction subsystem adapted to receive patient position data corresponding to the first and second image data sets and device position data corresponding to the first and second image data sets, and the motion correction subsystem is operable to measure a change in relative position between the patient and the imaging device and, upon detecting a change in the relative position, compensate in at least one of the first image data set and the second image data set for the change in relative position, prior to performing the digital subtraction operation.

12. The medical imaging system of claim 11 wherein the imaging device includes an image source operable to emanate radiation towards the patient and an image receiver positioned to receive radiation from the image source.

13. The medical imaging system of claim 11 wherein the imaging device is selected from the group consisting of an x-ray imaging device, a computed tomography imaging device and a magnetic resonance imaging device.

14. The medical imaging system of claim 11 wherein the tracking subsystem is further defined as an infrared tracking sensor.

15. The medical imaging system of claim 11 wherein the imaging device further includes a plurality of tracking targets that are detectable by the tracking subsystem.

16. The medical imaging system of claim 11 further comprises a reference frame marker positioned in a fixed location relative to the patient, where the reference frame marker includes tracking targets that are detectable by the tracking subsystem.

17. The medical imaging system of claim 16 wherein the reference frame marker is physically attached to a portion of the patient.

18. The medical imaging system of claim 11 further comprising a surgical instrument having tracking targets that are detectable by the tracking subsystem, such that the tracking subsystem detects in real-time instrument position data indicative of the position of the surgical instrument.

19. The medical imaging system of claim 18 wherein the motion correction subsystem is adapted to receive instrument position data from the tracking subsystem and operable to compensate for a change in the position of the surgical instrument in at least one of the first image data set and the second image data set.

20. A method for performing a digital subtraction operation in a medical imaging device, comprising:

capturing a first image data set representative of a patient;

detecting first patient position data indicative of the position of the patient during acquisition of the first image data set;

detecting first device position data indicative of the position of the imaging device during acquisition of the first image data set;

capturing a second image data set representative of the patient;

detecting second patient position data indicative of the position of the patient during acquisition of the second image data set;

detecting second device position data indicative of the position of the imaging device during acquisition of the second image data set;

determining if a change occurs in the relative position between the patient and the imaging device during a time interval between the acquisition of the first image data set and the acquisition of the second image data set; and performing a digital subtraction operation between the first image data set and the second image data set, when no substantial change occurs in the relative position between the patient and the imaging device.

21. The method of claim 20 further comprises measuring the change in relative position between the patient and the imaging device, and performing the digital subtraction operation when the measured change in relative position is less than a predetermined threshold value indicative of a maximum acceptable change in the relative position between the patient and the imaging device.

22. The method of claim 20 further comprises compensating at least one of the first image data set and the second image data set for a change in relative position between the patient and the imaging device prior to performing the digital subtraction operation.

23. The method of claim 22 further comprises compensating at least one of the first image data set and the second image data set when the measured change in relative position exceeds a predetermined threshold value indicative of a maximum acceptable change in the relative position between the patient and the imaging device.

24. The method of claim 22 wherein the step of compensating at least one of the first image data set and the second image data set further comprises performing a translational correction to at least one of the image data sets when the change in relative position between the patient and the imaging device is parallel to an image plane of the imaging device.

25. The method of claim 22 wherein the step of compensating at least one of the first image data set and the second image data set further comprises performing a scaled correction to at least one of the image data sets when the change in relative position between the patient and the imaging device is perpendicular to an image plane of the imaging device.

26. The method of claim 22 wherein the step of compensating at least one of the first image data set and the second image data set further comprises performing a rotational correction to at least one of the image data sets when the change in relative position between the patient and the imaging device is rotational to an image plane of the imaging device.

* * * * *